United States Patent [19]

Scott

[11] Patent Number: 4,650,499

[45] Date of Patent: Mar. 17, 1987

[54] GAS CHROMATOGRAPHIC APPARATUS AND METHOD

[75] Inventor: Richard L. Scott, Bartlesville, Okla.

[73] Assignee: Phillips Petroleum Company, Bartlesville, Okla.

[21] Appl. No.: 802,494

[22] Filed: Nov. 27, 1985

[51] Int. Cl.$^4$ .................. B01D 15/08; G01N 31/04
[52] U.S. Cl. .................................. 55/18; 55/67; 55/197; 55/270; 73/23.1; 422/80; 422/89; 436/161
[58] Field of Search .......... 55/18, 67, 197, 270, 55/386; 73/23.1; 422/78, 80, 89; 436/115, 123, 133, 149, 151, 158, 160, 161

[56] References Cited

U.S. PATENT DOCUMENTS

| | | | |
|---|---|---|---|
| 3,015,227 | 1/1962 | Barber, Jr. | 73/23 |
| 3,056,277 | 10/1962 | Brenner | 73/23 |
| 3,097,519 | 7/1963 | Favre | 73/23 |
| 3,111,849 | 11/1963 | Broerman | 73/422 |
| 3,223,747 | 12/1965 | Bohrer | 55/197 X |
| 3,425,807 | 2/1969 | Levy | 23/232 |
| 3,498,106 | 3/1970 | Fuller et al. | 73/23.1 |
| 3,514,262 | 5/1970 | Ayers | 23/230 |
| 3,518,059 | 6/1970 | Levy | 23/232 |
| 3,686,923 | 8/1972 | Favre | 73/23.1 |
| 3,698,869 | 10/1972 | Condon | 55/67 X |
| 3,807,217 | 4/1974 | Wilkins et al. | 73/23.1 |
| 3,960,520 | 6/1976 | Allen | 55/59 |
| 4,013,429 | 3/1977 | Sircar et al. | 55/33 |
| 4,181,006 | 1/1980 | DeFord | 73/23.1 |
| 4,234,315 | 11/1980 | Scott | 23/230 PC |
| 4,271,697 | 6/1981 | Mowery, Jr. | 55/67 X |
| 4,274,967 | 6/1981 | Snyder | 210/659 |
| 4,403,503 | 9/1983 | Banerjee et al. | 73/23.1 X |
| 4,467,038 | 8/1984 | Scott | 436/115 |

OTHER PUBLICATIONS

"Optichrom ® 2100 Process Chromatograph System", Company Brochure from Applied Automation, Inc., Bartlesville, Okla.
"Ten Port Multi-Functional Sampling Valves", Product Bulletin from Valco Instruments Co., Houston Tex.

Primary Examiner—Robert Spitzer
Attorney, Agent, or Firm—William R. Sharp

[57] ABSTRACT

A gas chromatographic method and apparatus are provided wherein a reservoir system including at least one reservoir is utilized to collect each component as it elutes from a chromatographic separation column. Immediately after collection of each component, a constant flow of carrier gas is allowed to pass into the reservoir system to carry each component to a detector. According to another aspect of the invention, a method is provided which employs a reference gas mixture in conjunction with the reservoir system to check calibration of a gas chromatography system.

25 Claims, 7 Drawing Figures

GAS CHROMATOGRAPHIC APPARATUS AND METHOD

BACKGROUND OF THE INVENTION

This invention relates to a gas chromatographic apparatus and method wherein a constant flow rate is maintained during analysis of a sample. In another aspect, the invention relates to a method which is effective in checking or redetermining the calibration of a gas chromatographic apparatus quickly and easily.

Gas chromatography instruments for the chemical analysis of samples typically include a sampling means for ejecting the sample in vaporized form therefrom, a gas chromatography column for separating components of the vaporized sample, and a detector which detects the components as they elute from the column. An inert carrier gas is employed to sweep the gaseous sample through the column. Such an apparatus can also conveniently include a recording device which records the outlet of the detector in a conveniently readable form, such as peaks on a chart.

Each peak corresponds to a particular component and has an amplitude which is a function of concentration where a concentration sensitive detector is used. In addition, an area, denoted simply as peak area, is defined under each peak which is representative of the amount (i.e., in grams) of its corresponding component in the sample. Stated another way, peak area is the integrated output of the detector for a particular detected component.

Ideally, peak area should vary solely in response to a change in the amount of the component detected. In actual practice, however, peak areas also change in response to changes in extraneous conditions such as temperature, barometric pressure and flow rate into the detector. Thus, any change in any one of these conditions during analysis can lead to erroneous results. It is, therefore, important that all extraneous conditions be maintained substantially constant to the extent possible.

Maintenance of a constant flow rate into the detector has been a particularly critical problem in prior gas chromatography systems. There are two primary causes for undesirable changes in flow rate. First, the flow rate of a component tends to vary according to the component concentration as the component elutes from the separation column. Second, a component in the column will tend to unpredictably affect the flow rate of another component which has already exited the column. This is known as the "slugging" effect.

Another important problem in gas chromatographic analysis is the nonlinear response of virtually all detectors. That is, the amplitude of the detector's output signal is not a linear function of the parameter, such as concentration, being detected. This also means that peak area is typically a nonlinear function of the amount of the corresponding component in the sample. Such nonlinearity dictates that calibration be carried out in order to obtain accurate results.

Prior calibration techniques have typically involved eluting a number of standard samples of known mass through the separation column, and then determining the peak area corresponding to each standard sample. A calibration curve is then plotted by plotting a point for each sample, wherein each point has a first coordinate corresponding to the ratio between a quantitative measurement (i.e., mgs of carbon) of the sample and peak area, and a second coordinate corresponding to peak area. A calibration factor can be derived for any peak area which can be used to determine the actual amount of a component associated with a particular peak.

The above described calibration technique is very slow and tedious to carry out since each standard sample must be individually weighed or volumetrically measured, and since each vaporized standard sample must then be passed through the separation column.

SUMMARY OF THE INVENTION

It is, therefore, an object of the invention to provide a gas chromatographic apparatus and method wherein the flow rate of separated components into the detector can be maintained substantially constant during detection of each component.

It is also an object of the invention to provide a method which enables a quick and easily implemented calibration check of a gas chromatography instrument, and which can also be used to obtain a calibration curve.

The first mentioned object is realized by a method which comprises chromatographically separating a sample gas mixture into a plurality of components with a separation column, each of the components being eluted from the separation column in sequence; sequentially collecting each of the eluted components in a reservoir system which includes at least one reservoir, only one component being in a reservoir at any one time; flowing a carrier gas into the reservoir system immediately after collection of each component as to sequentially carry each component from the reservoir system and directly into a detector, wherein the flow rate into the detector is substantially costant during the step; and detecting each component with the detector. This method effectively avoids the above-described unpredictable flow patterns associated with the separation column by employing an independent and controlled flow of carrier gas to move each component through the detector. A substantially constant flow rate is thereby obtained during detection of the components, thus improving accuracy of sample analysis.

According to another aspect, a method is provided which comprises: filling a reservoir with a reference gas mixture which comprises an inert gas and a particular concentration of a standard gas; flowing a carrier gas of the same composition as the inert gas into the reservoir so as to carry the reference gas mixture from the reservoir and into a detector which is reponsive to the concentration of the standard gas, at least a portion of the gas flowing into the detector being pure reference gas mixture so as to have the standard gas therein in the above-mentioned concentration. This method can be used to quickly and easily recalibrate or merely check the calibration of a gas chromatography system. The method does not require that a sample be passed through a separation column, and also does not require slow and tedious weighing or volumetric measurement of standard samples. Such measurements require independent calibrations of their own and have the problems associated with possible leaks and contamination.

According to yet another aspect of the invention, an apparatus is provided which comprises:

a gas chromatographic separation column capable of separating components of a sample gas mixture; a first reservoir; a second reservoir; first means for defining a flow path which extends between the outlet of the column and the inlets of the first and second reservoirs;

detector means capable of detecting components received therethrough; second means for defining a flow path which extends between the inlet of the detector means and the outlets of the first and second reservoirs;

first valve means associated with the first and second flow path defining means, the first valve means being adapted to provide selective fluid communication between the column outlet and the first reservoir inlet, between the column outlet and the second reservoir inlet, between the first reservoir outlet and the detector means inlet and between the second reservoir outlet and the detector means inlet;

a carrier gas source having an outlet; third means for defining a flow path which extends between the carrier gas source outlet and the inlets of the first and second reservoirs;

second valve means associated with the third flow path defining means and being adapted to provide selective fluid communication between the carrier gas source outlet and the first reservoir inlet, and between the carrier gas source outlet and the second reservoir inlet. The apparatus can also include two reference gas sources for providing a flow of two different reference gases to the reservoirs. The apparatus is useful in performing the above described methods, and is particularly advantageous in view of the fact that it can be used to collect and detect any number of components with only two reservoirs and one detector.

DESCRIPTION OF THE PREFERRED EMBODIMENTS

A preferred embodiment of the invention will now be described with reference to the Figures. It should be understood that although this embodiment is described in terms of a CHNS (carbon, hydrogen, nitrogen and sulfur) chromatography system, the invention could be applied to any other type of gas chromatography system wherein components in a sample are separated and subsequently detected.

Figure 1:
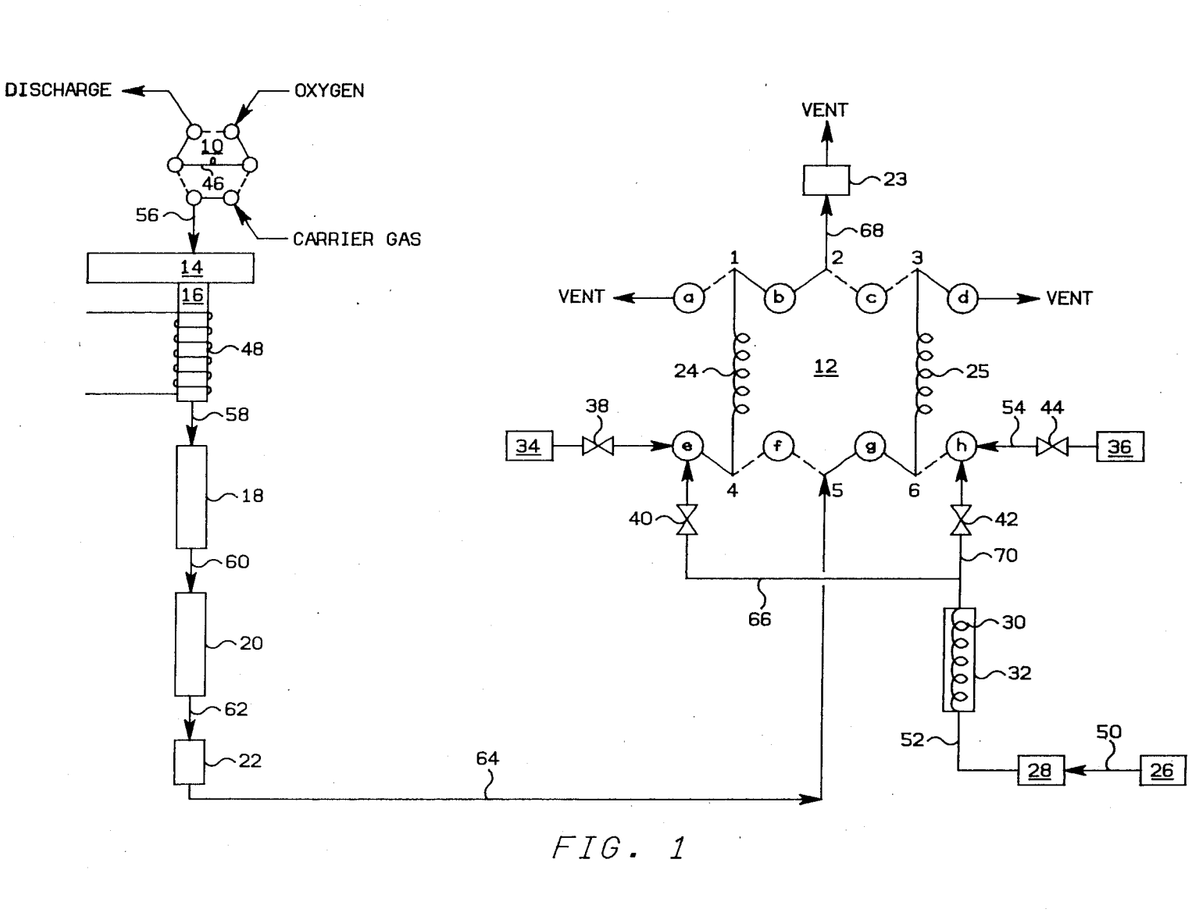
FIG. 1 is a schematic representation of a gas chromatography apparatus, which includes two reservoirs, according to an embodiment of the present invention.

Referring now to FIG. 1, the illustrated apparatus includes multi-port valves 10 and 12; sample introduction means 14; combustion chamber 16; reduction chamber 18; chromatographic separation column 20; detectors 22 and 23; a reservoir system which comprises reservoirs 24 and 25; carrier gas source 26; pressure regulator 28; fixed resistance coil 30 and associated oven 32; reference gas sources 34 and 36; and valves 38, 40, 42 and 44.

Each of the multi-port valves are two positions shown diagramatically with small circles representing the ports and straight lines between the ports representing passages in the core. The dashed straight lines represent passages open to flow in the first valve position and the solid lines represent those passages open to flow in the second valve position. Valve 10 includes six ports, and a loop 46 connects two of the ports. Valve 12 includes eight ports which are designated a-h, and are hereafter referred to by valve number and port letter. For example, port a valve 12 is referred to as port 12a. Valve 12 also includes twelve passages which interconnect various ports as shown. Pairs of passages connect at connection points 1-6, and are hereafter referred to by the port designation and connection point. Further by way of example, the passage extending between port 12a and connection point 1 is denoted as passage 12a-1. Although multi-port, multi-passage type valves are used in the illustrated embodiment, many other types of valves can be used to direct gas flows as desired.

Automatic operation of valves 10 and 12, and also 38, 40, 42 and 44, can be achieved by a programmable timing means and valve actuators (not shown) as is well known to those skilled in the art. Reference is made, for example, to U.S. Pat. Nos. 4,234,315 and 4,467,038.

Sample introduction means 14 can be a conventional indexing sample holder provided with suitable means for sealing inlet and outlet passages.

Combustion chamber 16 is heated by a coil 48. The combustion chamber is typically maintained at a temperature of about 1000° C. to obtain rapid, essentially complete combustion of a sample. Such combustion yields a sample gas mixture which includes water, sulfur dioxide, carbon dioxide and nitrogen components, and also some undesirable products referred to below.

Reduction chamber 18 is preferably constructed of copper, and is maintained at a temperature of about 850° C. for the reduction of some undesirable combustion products (such as $NO_x$ to $N_2$) and for the consumption of excess oxygen.

Separation column 20 can be a conventional temperature programmed column capable of separating components of a sample gas mixture. The column can be packed, by way of example, with Poropak T or Q and Carbowax on Teflon.

Detectors 22 and 23 are preferably thermal conductivity detectors. Such a detector provides an output signal representative of the difference in thermal conductivity of column effluent and the carrier gas. The temperature difference between resistance elements can be measured by an electrical bridge circuit, such as a wheatstone bridge. In addition, a thermal conductivity detector is concentration sensitive, i.e., the output signal depends on the degree of dilution of the sample components in the carrier gas, or stated another way, depends on the concentration of the sample components in the carrier gas. The instantaneous response of these types of detectors are also sensitive to various extraneous conditions such as temperature and barometric pressure as noted above, but their instantaneous response, or output signal, is essentially independent of flow rate. However, their integrated response (or peak area) varies inversely with flow rate, thus making a constant flow rate into the detector desirable in order to obtain accurate results. Although thermal conductivity detectors are preferred for use with the invention, other types of detectors, such as infrared and fluorescent detectors, can be employed according to certain aspects of the invention.

As will become more apparent below, detector 22 is utilized solely as a "rough" detector to assist in the proper timing in operating the various valves.

As shown, the inlet of reservoir 24 is connected to connection point 4 of valve 12, and the outlet is connected to connection point 1. Likewise, the inlet and outlet of reservoir 25 are connected to connection points 6 and 3 respectively. Reservoirs 24 and 25 are preferably coiled tubes of relatively great length compared to inner diameter. Typical inner diameter are in the range of about 1/10-⅜ inch, most preferably about ⅛-½ inch. The length of each reservoir is typically between about 20 and about 50 feet. One can determine the minimum length of each reservoir by, for example, noting the time necessary for the largest component of interest to elute from the column and applying the formula $L=(4FT\pi/D^2)$, where L is the length of the reservoir in cm, D is the inside diameter of the reservoir in cm, F is the rate of carrier gas flow (through the column) in ml/min, and T is the time for peak elution from the column. Stated most generally, the dimensions of each reservoir are preferably sufficient to retain the entirety of the column effluent component, being collected in a respective reservoir, which has the greatest volume. Suitable materials for the reservoirs include stainless steel, Teflon and glass, although any material inert to the chemicals being analyzed could be used. It is also preferable that the reservoirs be in a temperature controlled environment wherein the temperature is sufficiently high to avoid water condensation, but low enough to avoid an undue loss of detector sensitivity due to heating of gases in the reservoirs. In view of these considerations, the temperature of the reservoirs is preferably maintained in the range of about 50° C. to about 100° C.

Fixed resistance coil 30 preferably comprises a coiled tube of a material, such as quartz or glass, which is relatively insensitive to temperature changes so as to not change in dimensions in response to temperature changes. This is desirable in order to avoid flow rate changes which can result from contraction or expansion of coil 30. Other materials like copper or steel could also be utilized, but are not preferred due to their inferior temperature sensitivity. By way of example, coil 30 can have a length of about 10 feet and inside diameter of about ¼ inch. Coil 30 is also preferably packed with quartz or glass beads, (i.e. about 100 mesh) or chips of firebrick, but could alternatively be unpacked providing a smaller diameter tube is used. Oven 32 is provided to maintain coil 30 at a constant temperature, most typically in the range of about 50° C. to about 80° C., to further ensure against any contraction of expansion of coil 30 and packing material therein. It is also preferred that the coil be dimensioned and suitably packed to provide a pressure differential of about 30-40 lbs/in² across the coil so that the pressure at its outlet is approximately at atmospheric pressure to allow convenient venting to the atmosphere after detection of the gaseous components.

Carrier gas source 26, typically a conventional gas cylinder, delivers an inert carrier gas such as helium to pressure regulator 28 via line 50. Pressure regulator 28 is employed to provide carrier gas through line 52 to the inlet of coil 30 at a constant pressure of about 50 lbs/in². Constant pressure at the inlet of coil 30 gives a constant flow rate at its outlet since its resistance to flow is substantially fixed. Therefore, use of pressure regulator 28 and fixed resistance coil 30 serves to provide a constant flow rate, preferably varying from the desired rate only a few tenths of a percent, to detector 23 when there is fludi communication between the carrier gas source outlet and the detector inlet. It should be understood, however, that any means for maintaining such a constant carrier gas flow rate could be employed according to the invention, such as an arrangement which includes a conventional flow controller.

Reference gas sources 34 and 36 deliver a reference gas mixture, later defined, through respective outlets thereof. The reference gas mixtures are utilized for calibration as will become more apparent in the description of apparatus operation.

Various lines (or conduits) and valve passages together with certain elements of the apparatus define various flow paths which extend between elements of the apparatus. Valves associated with the flow paths provide selective fluid communication between the various elements. For example, line 54, which extends between reference gas source 36 and valve port 12h, defines a flow path with valve passage 12h-6 which extends between the inlet of reservoir 25 and the outlet of reference gas source 36. Valve 44 cooperates with valve port 12h to provide selective fluid communication between the outlet of carrier gas source 36 and the inlet of reservoir 25. A similar arrangement is provided with respect to reference gas source 34 and reservoir 24.

Operation according to a preferred embodiment will now be described with reference to FIG. 1. First, a sample of a material to be analyzed is introduced into combustion chamber 16 through sample introduction means 14. Carrier gas is introduced into combustion chamber 16 via sample introduction means 14, line 56 and valve 10. A measured volume of oxygen in loop 46 is then supplied via a valve port as shown at a suitable pressure to the combustion chamber. The oxygen is swept into combustion chamber 16 by the carrier gas.

Combustion of the sample gas takes place in combustion chamber 16 so as to produce combustion products, which include carbon dioxide, sulfur oxides, water, nitrogen and nitrogen oxides. The combustion products are swept by the carrier gas via line 58 through reduction chamber 18, in which the reduction of $SO_3$ and nitric oxides to $SO_2$ and nitrogen respectively, and also consumption of excess oxygen, occurs.

The products of combustion as processed by the reduction chamber, herein denoted as the sample gas mixture, are swept into separation column 20 through line 60. The sample gas mixture entering the column includes carbon dioxide, water, nitrogen and sulfur dioxide. These components of the gaseous mixture are separated by the column in a conventional fashion so that each component elutes from column 20 in sequence, each component being passed through line 62 to detector 22 which acts to detect each component as it elutes from column. Starting with the first component, this component is received by valve 12 via line 64.

In the immediately following discussion, valve 12 is assumed to be in the first position, (dashed lines being open to flow), and valves 38 and 44 are assumed to be closed, in which case valves 40 and 42 may remain open in such an operational mode wherein no calibration is being preformed with the reference gas mixtures.

It is emphasized again at this point that all valve switching may be carried out by means of an appropriate programmable timing means which is adapted to receive signals from detector 22, wherein the timing means responds to the appropriate output signals of detector 22 as programmed into the timing means. The timing means can provide signals to valve actuators for switching valve positions. Alternatively, an appropriate chart recorder can be connected to detector 22 for indicating the peaks as they are detected. An operator can visually monitor the peaks in this manner and switch valves at the correct times.

With valve 12 in the first position, the first component is swept by the carrier gas into reservoir 24 via passages 12f-5 and 12f-4, and valve port 12f. As the first component is being collected, carrier gas or other gases remaining in reservoir 24 from a previous operation are allowed to flow from the outlet of reservoir at connection point 1 to vent through passage 12a-1. During collection of the first component in this manner, carrier gas from coil 30 is allowed to pass through reservoir 25 to detector 23. Valve 12 is left in the first position until the entire first component is collected in reservoir 24, at which time valve 12 is switched to the second position. The correct time for switching is determined from the outlet signal of detector 22 which will indicate the end of the peak corresponding to the first component. An appropriate lag time is allowed for passage of this portion of the component peak through line 64. This lag time can be estimated or calculated utilizing flow rate, volume available for flow, etc. Most conveniently, line 64 is as short as possible to avoid such lag time problems.

It is preferred that the various components are sufficiently separated as they elute from the column in order to minimize the possibility of collecting a portion of the second component in reservoir 24 before switching a valve 12 occurs. Spreading of the components and associated peaks can be easily accomplished by lengthening the column, lowering the temperature of the column, or by changing the column packing materials. By spreading the component peaks apart to some degree, the correct time for switching of valve 12 becomes far less critical, since the time interval between collection of one component and arrival of the next component is greater.

With valve 12 in the second position, and immediately after collection of the first component in reservoir 24, highly controlled flow of carrier gas at a constant flow rate in the range of about 100 to about 200 cc/min passes into reservoir 24 from the outlet of coil 30 via line 66, valve port 12e and valve passage 12e-4. It should be noted in particular that the carrier gas flow from coil 30 into reservoir 24 is independent from carrier gas flow for the separation column, wherein the carrier gas from coil 30 passes directly into reservoir 24 without passing through the separation column. The carrier gas carries the first component from the outlet of reservoir 24, through passages 12b-1 and 12b-2, and through line 68 directly into detector 23. At the same time that carrier gas flow is allowed to pass into reservoir 24, reservoir 25 is available for collection of the second component. The second component preferably arrives at the inlet of reservoir 25 a short time after switching of valve 12 to the second position occurs. As noted above, this type of timing scheme is preferable over one where arrival of the second component at valve 12 occurs nearly simultaneously with the switching of valve 12. Collection of the second component typically begins, however, during the passage of carrier gas through reservoir 24, such collection in reservoir 25 occurring substantially as discussed with respect to reservoir 24 and the first component via valve passages 12g-5 and 6. Collection of the second component typically ends after the entirety of the first component has passed from reservoir 24.

Of course, it is possible that a collected component could be carried from a reservoir before arrival of the next component, in which case only one reservoir could be employed as an alternative to the illustrated embodiment. Such an arrangement, however, would require substantial separation in time between the components, and would thus substantially and undesirably increase analysis time.

After collection of the second component in reservoir 25 is completed, valve 12 is switched back to the first position so as to allow carrier gas to carry the second component to detector 23 via valve passages 12h-6, 12c-3, 12c-2 and line 68. The third component is collected in reservoir 24 while valve 12 is in the first position. In a similar manner as discussed with regard to the first and second components, the third component is carried to detector 23 by the carrier gas, and the fourth component is collected in reservoir 25, and subsequently passed into detector 23.

The above described apparatus and method for the detection of chromatographically separated components have several distinct advantages associated therewith. First, utilizing the independent and highly controlled flow of carrier gas as described enables the flow of each component into the detector at a constant flow rate so as to avoid the erroneous results associated with a varying flow rate during analysis. The apparatus and method achieve this distinct advantage by isolating the outlet flow of the separation column from the detector. Thus, varying flow rate due to peak elution from the column and due to the above-mentioned slugging effect, involving the effect on flow rate by a component still in the column, is substantially avoided by the present invention. Since the present invention permits the use of a crude separation of components with a varying column outlet flow rate, a single temperature controlled column and a single detector may be used to obtain accurate results instead of, for example, several isothermal columns and several corresponding detectors.

A fast and easily implemented calibration of detector 23 can be accomplished utilizing the illustrated apparatus as follows. According to this aspect of the invention, detector 23 should be responsive to concentration. A thermal conductivity detector is preferred.

With respect to reference gas source 34 and 36, these sources deliver reference gas mixture through outlets thereof, wherein each reference gas mixture comprises an inert gas of the same composition as the carrier gas and a known concentration of a standard gas, most typically $CO_2$. The concentration of the standard gas in each reference gas mixture is preferably in the general range of component concentrations to be expected during analysis. Also, the concentrations of standard gases in the reference gas mixtures are preferably different from one another, the two concentrations being sufficiently different to allow a determination of the calibration curve as will become more apparent below. For the sake of illustration, the first reference gas mixture will be assumed to be associated with source 36 and to have the higher concentration (i.e., several hundred ppm or about 0.05–0.1 mg/ml of reference gas) of standard gas, and the second reference gas mixture will be assumed to be associated with source 34 and to have the lower concentration (i.e., only several ppm or about 0.0001–0.0005 mg/ml of reference gas) of standard gas.

For the purpose of this discussion of calibration, valves 40 and 42 will be assumed to be closed unless stated otherwise, and it will also be initially assumed that there is no effluent flowing from the column for the sake of simplicity.

Assuming valve 12 to be in the first position, the first reference gas mixture is first allowed to flow into reservoir 25 from source 36 via line 54 and passage 12h-6 by opening valve 44, the first reference gas flowing through reservoir 25, passages 12c-2 and 3, and line 68 to detector 23. Such flow is allowed to continue, for a period of several seconds for example, until all gases originally contained in reservoir 25 are displaced, leaving only pure first reference gas mixture in the reservoir. This operation is a convenient way of filling reservoir 25 with the first reference gas mixture using the illustrated apparatus, although other techniques are certainly possible with other types of valving, such as allowing reference gas to pass to vent during filling of the reservoir.

Valve 44 is then closed, and valve 42 is opened to allow carrier gas to flow into reservoir 25 via line 70 so as to carry the pure slug of first reference gas to detector 23. According to the invention, there is no need for the reference gas mixture to flow through the separation column. Of course, some of the pure reference gas at the lower end of reservoir 25 will be diluted by the flow of carrier gas. Such dilution will also occur at the upper end of reservoir 25. It is important that reservoir 25 be long enough to ensure that at least a portion of the gas flowing into detector 23 is pure first reference gas mixture having the standard gas therein in the known concentration. This pure slug of reference gas is necessary, as will become more apparent, to allow the detection of the known concentration of standard gas in the pure reference gas, the corresponding detected peak being essentially a square wave. It should also be noted at this point that the inert gas in either reference gas mixture should be the same composition as the carrier gas because if different compositions were used, differentiation between detection of the inert gas and the desired detection of the standard gas would be impossible.

After passage of the entire slug of first reference gas mixture from reservoir 25, as is adequately indicated by detector 23, valve 12 is switched to the second position and valve 38 is opened to allow the second reference gas mixture to flow through reservoir 24 and detector 23 so as to fill reservoir 24 with the second reference gas mixture. Valve 38 is then closed, and valve 40 opened to allow carrier gas to carry a pure slug of the second reference gas mixture into the detector 23 for detection accordingly. Valve 40 is then closed.

According to this simple mode of operation, it is preferred that carrier gas is allowed to continue for a time after detection of the final reference gas mixture so that the detected peaks corresponding to the reference gas mixtures are distinctly separated.

Figure 2:
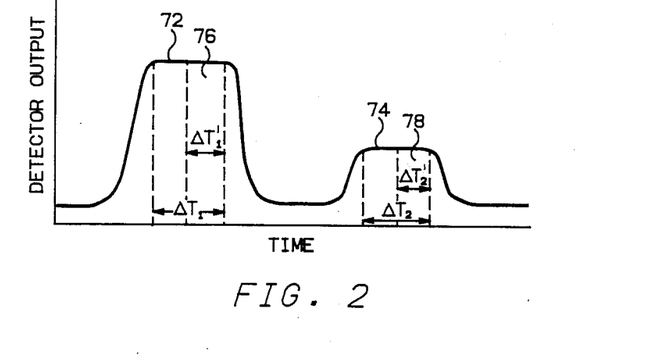
FIG. 2 is a graphical plot of peaks corresponding to two different concentrations of standard gas in two reference gas mixtures.

Referring now to FIG. 2, peaks are shown which can be expected according to the above mode of operation. Peak 72 is the peak corresponding to the first reference gas mixture, and peak 74 corresponds to the second reference gas mixture. Each peak has, as shown, a square wave portion indicated by dashed lines. The sloped portions of the peaks correspond to volumes of reference gas mixture at each end of the pure slug where dilution of the reference gas by the carrier gas has occurred.

The square wave portions of the peaks can be utilized to obtain a calibration curve. First, the square wave portions of the peaks are known to correspond to the pure reference gas slugs. Thus, the amplitudes of these square wave portions correspond to the known standard gas concentrations since the detector's instantaneous output varies with concentration of the standard gas according to this aspect of the invention. The time intervals for the square waves are also known, as indicated to be $\Delta T_1$ and $\Delta T_2$ corresponding to peaks 72 and 74 respectively.

Note from above, however, that a first portion of each square wave corresponds to flow of reference gas through detector 23 directly from its respective reference gas source during filling of the reservoir. This uncontrolled flow rate cannot be relied on for calibration. A second portion of each square wave corresponds to the controlled and known flow rate from coil 30. $\Delta T_1'$ and $\Delta T_2'$ are the time intervals associated with these portions of the square waves for peaks 72 and 74 respectively. The exact times at which time intervals $\Delta T_1'$ and $\Delta T_2'$ begin can be easily determined from the times at which carrier gas flow from coil 30 is commenced.

The volume of pure reference gas mixture corresponding to the square wave portions having intervals $\Delta T_1'$ and $\Delta T_2'$ can be determined from the formula: $F\Delta T' = V$, where F is flow rate, $\Delta T'$ is the time interval and V is volume, wherein the formula can be applied to each square wave portion. As noted above, the flow rate F is known to be the constant flow rate of carrier gas from coil 30.

A quantitative measurement, in this case mass, of the standard gas for each pure reference gas mixture volume corresponding to $\Delta T_1'$ and $\Delta T_2'$ can be determined from the formula: $CV = M$, where C is the known concentration of standard gas in the reference gas mixture, V is the volume of reference gas mixture and M is the mass of standard gas therein.

The peak areas of square wave portions 76 and 78 can be determined from the product of amplitude and $\Delta T'$.

Figure 3:
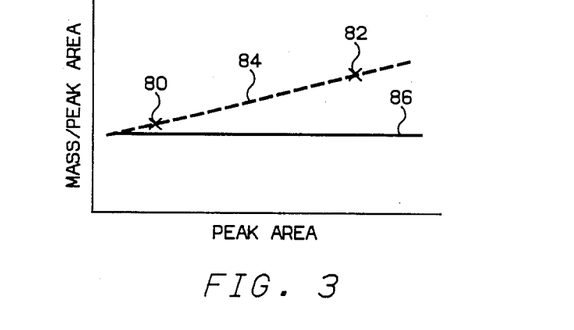
FIG. 3 is a graphical plot of a calibration curve which can be expected according to the invention.

Thus a calibration curve can be plotted from the above information. Referring to FIG. 3, a graphical plot of mass/peak area versus peak area is shown. A point 80 can be plotted for the second reference gas mixture having the lower concentration of standard gas, and point 82 can be plotted for the first reference gas mixture having the higher concentration of standard gas. A dashed line 84 is drawn through points 80 and 82 as a calibration curve. Of course, the actual calibration curve is probably not a straight line, but this gives a quick approximation of the calibration curve. Line 86 represents the ideal situation wherein the detector is linear, and where the ratio mass/peak area is a constant for all peak areas. The curve 84 shows that this is not the case so that peak area is not exactly proportional to mass for all peak areas. This condition must be taken into account during analysis. A calibration factor can be derived from the calibration curve for a particular sample component peak area as is well known in the art. This calibration factor can then be used to obtain the correct mass which corresponds to the peak area detected.

The above described method can be conveniently applied in conjunction with sample analysis to determine if the calibration curve, previously determined more accurately for example by a conventional technique, has shifted in position. Such a slight change in the calibration curve can occur due to a change in an extraneous condition such as barometric pressure, temperature or detector power supply outlet voltage. The type of condition change one is concerned with here is sustained change in a condition. Such a condition change might occur, for example, if a cold front moves into the area, thus leading to a change in barometric pressure. During a series of sample analyses taking place automatically over an extended period of time, commonly a day or more, determination of a change in the calibration curve due to such a change in conditions is a valuable tool in enhancing the accuracy of the final analysis results.

In a series of runs with many different samples, the calibration curve can be conveniently checked or redetermined in each run by collecting and detecting the first and second reference gas mixtures in the manner previously discussed immediately before, during (i.e., between sample peaks) or immediately after the separation and detection of the sample component peaks.

Referring again to FIG. 1, according to one embodiment, a particular run can begin with collection of the first component in reservoir 24 with valve 12 in the first position. While the first component is being collected, the first reference gas mixture is allowed to flow through reservoir 25 by opening valve 44 until the reservoir is full of pure reference gas. Valve 44 is then closed and valve 42 is opened to allow a flow of carrier gas to carry the slug of pure reference gas in reservoir 25 to detector 23 to be detected in a manner previously discussed. Following collection of the first component in reservoir 24, valve 12 is switched to the second position for collection of the second component and flow of the first component into detector 23. The remaining components are collected and detected similarly, wherein valve 12 is in the first position immediately after detection of the last component. Valve 12 is switched to the second position, and valve 38 is opened to permit the second reference gas mixture to flow through reservoir 24, followed by closure of valve 38 and opening of valve 40 to allow carrier gas to flow into reservoir 24 so as to carry a slug of pure second reference gas mixture to detector 23.

Figure 4:
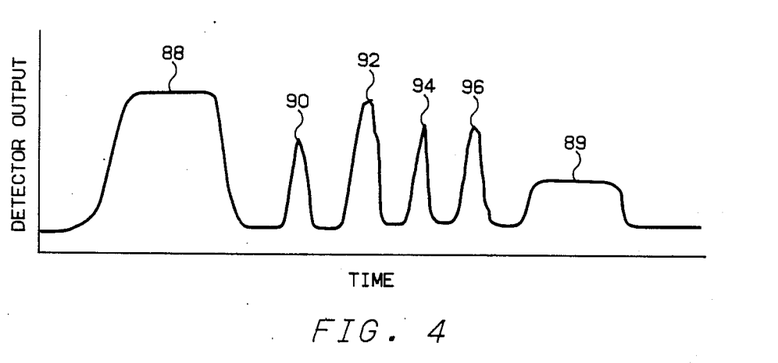
FIG. 4 is a chromatogram showing sample component peaks and standard gas peaks according to one embodiment of the invention.

Thus, the above described mode of operation produces a square wave corresponding to the first reference gas mixture immediately prior to detection of the first component, and a square wave corresponding to the second reference gas mixture immediately after detection of the last component. A graphical plot of such peaks are shown in FIG. 4, wherein 88 and 89 indicate the two reference gas peaks, and wherein 90, 92, 94 and 96 indicate the $N_2$, $CO_2$, $SO_2$ and $H_2O$ peaks respectively.

It should be understood that it is not necessary to actually plot calibration curve points such as in FIG. 3 to merely check the calibration curve in conjunction with a run. It is within the scope of the invention to merely detect the maximum peak amplitude (which is a function of concentration) for both, or for only one reference gas mixture. A change in detected maximum amplitude will indicate a change in extraneous conditions and a consequent shift of the calibration curve since it is known that the maximum peak amplitude corresponding to the square wave peak portion is associated with a particular, constant standard gas concentration. Any change in maximum amplitude can be monitored, and a corresponding shift in the calibration curve estimated. Therefore, it is not necessary that the standard gas concentration be known where calibration is being checked.

Figure 5:
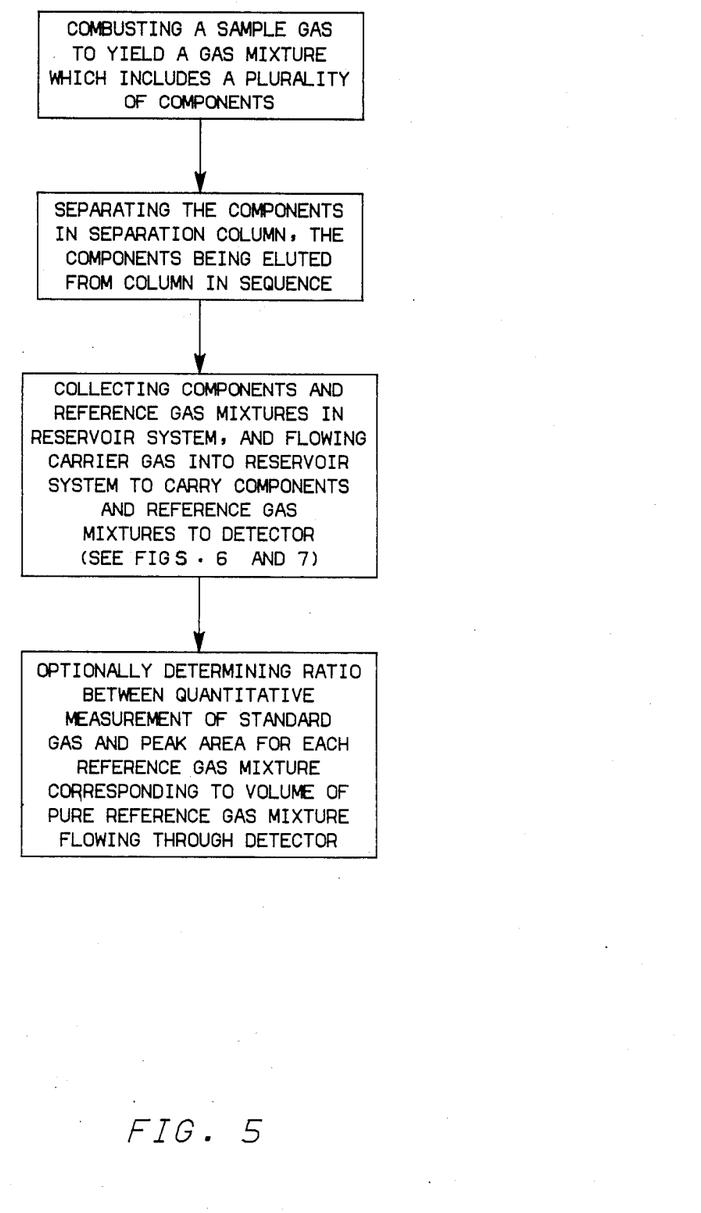
FIG. 5 is a flow chart outlining various steps of an embodiment of a method according to the invention.

Referring now to FIG. 5, there is shown a flow chart outlining steps of the above-described method utilizing two reference gas mixtures for producing standard gas peaks before and after detection of the sample component peaks. As shown, a ratio can optionally be obtained for the purpose deriving a rough calibration curve and recalibrating accordingly.

Figure 6:
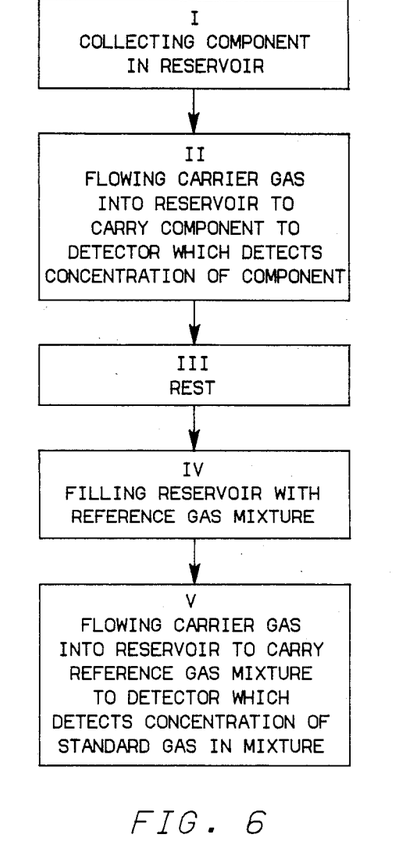
FIG. 6 is a flow chart giving further details of steps shown in FIG. 5.

Referring to FIG. 6, there is shown another flow chart which sets forth the steps involved for a particular reservoir (either reservoir 24 or 25) with respect to collection of components and reference gas mixtures. Each box corresponds to a step, and is designated by a roman numeral.

Figure 7:
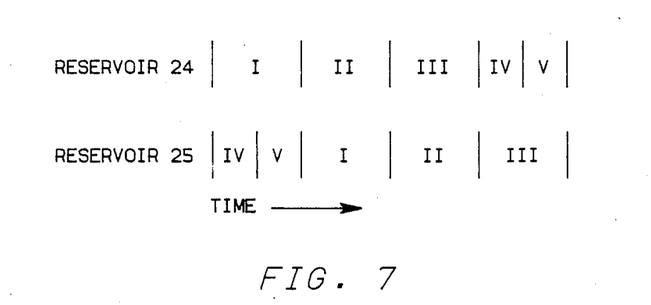
FIG. 7 is a diagram showing the sequence of steps shown in FIG. 6 for each reservoir shown in FIG. 1.

Referring to FIG. 7, a diagram is shown which illustrates one time sequence of steps from FIG. 6 for both reservoirs. Each step in the diagram is indicated with roman numerals. The sequence of steps illustrated corresponds to a simplified case wherein only two components are collected.

Many modifications of the present invention are possible, as will be apparent to one skilled in the art, without departing from the spirit and scope thereof. For example, a reservoir could be provided for each sample component, along with a detector for each reservoir. One other possible modification could involve the addition of a third reservoir to the FIG. 1 apparatus for the sole purpose of containing a reference gas mixture therein ready at all times (i.e., possibly between component peaks) for flow of the reference gas into the detector to check the calibration curve. According to yet another modification of the illustrated embodiment, two columns can be used instead of the single temperature programmed column illustrated. A first column utilizing, for example, 10% Carbowax on Teflon could be employed to retain water, and a second column using Poropak T could be utilized to separate the nitrogen, carbon dioxide and sulfur dioxide components. Carrier gas can be introduced between the columns after elution of nitrogen and carbon dioxide from the second column to backflush the water from the first column and to speed elution of sulfur dioxide from the second column. Such a mode of operation will greatly affect flow rates and thus lead to a rough "cutting" of components which is permitted by the invention.

That which is claimed:

1. A method comprising:
   (a) chromatograpically separating a sample gas mixture into a plurality of components with a separation column, each of the components being eluted from the separation column in sequence;
   (b) sequentially collecting each of said eluted components in a reservoir system which includes at least one reservoir, only one component being in a reservoir at any one time;
   (c) flowing a carrier gas into the reservoir system immediately after collection of each component so as to sequentially carry each component from the reservoir system and directly into a detector, wherein the flow rate into the detector is substantially constant during this step; and
   (d) detecting each component with the detector.

2. A method as recited in claim 1 wherein in step (c) the carrier gas flows directly into said at least one reservoir without passing through the separation column.

3. A method as recited in claim 1 wherein the reservoir system includes two reservoirs, the plurality of components including at least a first component and a subsequently eluted second component, and wherein in step (b) the first component is collected in one reservoir and the second component is collected in the other reservoir so as to alternate between reservoirs in the collection of components.

4. A method as recited in claim 3, wherein in step (c) the carrier gas is passed into said one reservoir after the collection of the first component in said one reservoir and at least partially during collection of the second component in said other reservoir.

5. A method as recited in claim 4, wherein said detecting step comprises detecting the concentration of each of said components in the carrier gas.

6. A method as recited in claim 5, further comprising the step of combusting a sample gas before step (a) to yield the sample gas mixture, the various components thereof including a water component, a sulfur dioxide component, a carbon dioxide component and a nitrogen component.

7. A method as recited in claim 1, further comprising the step of passing a reference gas mixture to the detector at a time when none of said components are flowing into the detector, the reference gas mixture comprising an inert gas of the same composition as the carrier gas and a particular concentration of standard gas.

8. A method as recited in claim 7, wherein said reference gas mixture is passed to the detector by a flow of carrier gas, at least a portion of gas flowing into the detector being substantially pure reference gas mixture having said concentration of standard gas therein.

9. A method comprising:
(a) filling a reservoir in a reservoir system comprising at least one reservoir with a volume of a first reference gas mixture, the first reference gas mixture comprising an inert gas and a particular concentration of a standard gas;
(b) flowing a carrier gas of the same composition as the inert gas into the reservoir after step (a) so as to carry the first reference gas mixture from the reservoir and into a detector responsive to the concentration of the standard gas, at least a portion of the gas flowing into the detector being substantially pure first reference gas mixture having the standard gas therein in substantially said particular concentration.

10. A method as recited in claim 9, wherein said method is carried out in a gas chromatography system which includes a separation column, said collecting step comprising flowing the first reference gas mixture into the reservoir without passing the first reference gas mixture through the separation column.

11. A method as recited in claim 9, wherein the detector generates an output signal having a maximum amplitude for a time $\Delta T$ during flow of said gas portion through the detector.

12. A method as recited in claim 11, further comprising the step of determining the product of $\Delta T$ and said maximum aplitude, said product being denoted as a peak area.

13. A method as recited in claim 12, wherein said particular concentration is a known concentration, and wherein gas flow through the detector is at a predetermined flow rate, said method further comprising the step of obtaining a quantitative measurement of the standard gas in said gas portion utilizing said known concentration, $\Delta T$ and said predetermined flow rate.

14. A method as recited in claim 13, further comprising the step of determining the ratio between the peak area and the quantitative measurement.

15. A method as recited in claim 9 further comprising the steps of: collecting a volume of a second reference gas mixture in a reservoir of the reservoir system, said second reference gas mixture having a standard gas therein in a concentration different from the concentration of standard gas in the first gas mixture; and passing carrier gas into the reservoir containing the second reference gas mixture so as to carry the second reference gas mixture into the detector.

16. A method as recited in claim 15, further comprising the steps of determining the peak area and quantitative measurement corresponding to said second reference gas mixture.

17. A method as recited in claim 15, further comprising the steps of separating a sample gas mixture into a plurality of components with the separation column and detecting the components with the detector, wherein said collector of the first and second reference gas mixtures and passing of the first and second reference gas mixtures into the detector is carried out immediately before, during, or immediately after said separating and detecting steps.

18. An apparatus comprising:
a gas chromatographic separation column having an inlet and an outlet, said separation column being capable of separating components of a sample gas mixture;
a first reservoir having an inlet and an outlet;
a second reservoir having an inlet and an outlet;
first means for defining a flow path which extends between said column outlet and each of said respective first and second reservoir inlets;
detector means capable of detecting components received therethrough, said detector means having an inlet;
second means for defining a flow path which extends between said detector means inlet and each of said respective first and second reservoir outlets;
first valve means associated with said first and second flow path defining means, said first valve means being adapted to provide selective fluid communication between said column outlet and said first reservoir inlet, between said column outlet and said second reservoir inlet, between said first reservoir outlet and said detector means inlet, and between said second reservoir outlet and said detector means inlet;
a carrier gas source having an outlet;
third means for defining a flow path which extends between said carrier gas source outlet and each of said respective first and second reservoir inlets;
second valve means associated with said third flow path defining means and being adapted to provide selective fluid communication between said carrier gas source outlet and said first reservoir inlet, and between said carrier gas source outlet and said second reservoir inlet.

19. An apparatus as recited in claim 18, wherein each of said first and second reservoirs comprises a coiled tubular member.

20. An apparatus as recited in claim 19, wherein said detector means is a thermal conductivity detector.

21. An apparatus as recited in claim 20, wherein said separation column is a temperature programmed gas chromatography column.

22. An apparatus as recited in claim 21, futher comprising means, disposed along said third flow path defining means, for maintaining a substantially constant flow rate into said detector means when there is fluid communication between said carrier gas source outlet and said detector means inlet.

23. An apparatus as recited in claim 22, further comprising a combustion means for combusting a sample gas to yield the sample gas mixture which includes a water component, a sulfur dioxide component, a carbon dioxide component and a nitrogen component.

24. An apparatus as recited in claim 18, further comprising: a first reference gas source for delivering a first reference gas mixture through an outlet thereof, the first reference gas mixture comprising an inert gas of the same composition as the carrier gas and a particular concentration of a standard gas; a fourth means for defining a flow path which extends between said first reference gas source outlet and said first reservoir inlet; and a third valve means, associated with said fourth flow path defining means, for providing selective fluid communication between said first reference gas source outlet and said first reservoir inlet.

25. An apparatus as recited in claim 24, further comprising: a second reference gas source for delivering a second reference gas mixture through an outlet thereof, the second reference gas mixture comprising an inert gas of the same composition as the carrier gas and a particular concentration of standard gas different from that concentration of standard gas in the first reference gas mixture; a fifth means for defining a flow path between said second reference gas source outlet and said second reservoir inlet; and a fourth valve means, associated with said fifth flow path defining means, for providing selective fluid communication between said second reference gas source outlet and said second reservoir inlet.

* * * * *